(12) United States Patent
Li et al.

US010131689B2

(10) Patent No.: US 10,131,689 B2
(45) Date of Patent: Nov. 20, 2018

(54) SEPARATION AND PURIFICATION METHOD FOR VANCOMYCIN HYDROCHLORIDE OF HIGH PURITY

(71) Applicant: Zhejiang Medicine Co., Ltd. Xinchang Pharmaceutical Factory, Xinchang County (CN)

(72) Inventors: Enmin Li, Xinchang County (CN); Yiyun Zhuang, Xinchang County (CN); Jue Wang, Xinchang County (CN); Xinqiang Sun, Xinchang County (CN); Xuejun Lao, Xinchang County (CN); Biwang Jiang, Xinchang County (CN)

(73) Assignee: Zhejiang Medicine Co., Ltd. Xinchang Pharmaceutical Factory, Xinchang County (CN)

( * ) Notice: Subject to any disclaimer, the term of this patent is extended or adjusted under 35 U.S.C. 154(b) by 75 days.

(21) Appl. No.: 15/033,116

(22) PCT Filed: Oct. 27, 2014

(86) PCT No.: PCT/CN2014/000950
§ 371 (c)(1),
(2) Date: Apr. 29, 2016

(87) PCT Pub. No.: WO2015/062168
PCT Pub. Date: May 7, 2015

(65) Prior Publication Data
US 2016/0264620 A1    Sep. 15, 2016

(30) Foreign Application Priority Data
Nov. 1, 2013 (CN) .......................... 2013 1 0537310

(51) Int. Cl.
*C07K 1/36* (2006.01)
*C07K 9/00* (2006.01)
*A61K 38/14* (2006.01)
*C07K 1/20* (2006.01)
*C07K 1/34* (2006.01)

(52) U.S. Cl.
CPC .............. *C07K 1/36* (2013.01); *A61K 38/14* (2013.01); *C07K 1/20* (2013.01); *C07K 1/34* (2013.01); *C07K 9/008* (2013.01)

(58) Field of Classification Search
CPC ... C07K 1/36; C07K 1/20; C07K 1/34; C07K 9/008; A61K 38/14
See application file for complete search history.

(56) References Cited

U.S. PATENT DOCUMENTS 5,223,413 A * 6/1993 Nagy .................... C07K 9/008
                                                            435/252.1
2010/0222252 A1* 9/2010 Xu ......................... A61K 38/14
                                                            514/3.1

FOREIGN PATENT DOCUMENTS

WO   WO 2006/061166    *  6/2006  ............... C07K 1/36

OTHER PUBLICATIONS

Sutherland (Filtration and Separation.com (2009), available at http://www.filtsep.com/view/717/what-is-nanofiltration/[Apr. 13, 2017 8:18:55 AM], accessed on Apr. 13, 2017, pp. 1-12).*
Vancomycin Hydrochloride, European Pharmacopoeia 5.0 (2005) 2670-2672.*
Hunter Whiteness Index, available at https://measuretruecolor.hunterlab.com/2015/04/23/what-is-hunter-whiteness-index/, accessed on Apr. 20, 2017.*
Amersham PRC Manual entitled Reverse Phase Chromatography, Principles and Methods, 1999, 86 pages.*
Technical Information sheet, obtained from https://www.hamiltoncompany.com/products/laboratory-products/hplc-columns/reversed-phase/polymeric-packings/prp-1, 2 pages, downloaded Jan. 21, 2018.*

* cited by examiner

*Primary Examiner* — Karlheinz R. Skowronek
*Assistant Examiner* — Joseph Fischer
(74) *Attorney, Agent, or Firm* — Ash Tankha; Lipton, Weinberger & Husick

(57) ABSTRACT

Provided is a separation and purification method for vancomycin hydrochloride of high purity. The method comprises the following steps: (1) obtaining a vancomycin hydrochloride solution from a crude vancomycin product by ion exchange chromatography and obtaining a concentrate by nanofiltration desalination and concentration; (2) adjusting the concentrate with a hydrochloric acid solution and then performing a column chromatography using a reverse chromatography column for the adjusted concentrate; (3) collecting the chromatographic solution of vancomycin to obtain a mixed chromatographic solution; (4) adjusting the mixed chromatographic solution, and separating the solution and the salts by nanofiltration desalination and concentration to obtain a concentrate; and (5) obtaining a vancomycin dry powder with a chromatographic purity of up to 99% and a pure white appearance by dehydrating and drying the concentrate of step (4), or by solvent crystallization or salting-out crystallization.

7 Claims, 6 Drawing Sheets

SEPARATION AND PURIFICATION METHOD FOR VANCOMYCIN HYDROCHLORIDE OF HIGH PURITY

FIELD OF THE INVENTION

The present invention relates to a separation and purification method for vancomycin hydrochloride of high purity. The method comprises performing a column chromatography of crude vancomycin product with a chromatographic purity 90% as raw material by using a SEPHADEX® column with salt-water as a mobile phase, and collecting a vancomycin hydrochloride with a chromatographic purity of more than 95%, separating solvent and salts by nanofiltration desalination and concentrating to obtain a concentrate of 100 mg/ml-200 mg/ml, and then performing a column chromatography using reverse C18 silica gel chromatographic column or reverse polymer chromatographic column, and eluting with methanol aqueous solution or ethanol aqueous solution containing ammonium salt as mobile phase, collecting vancomycin hydrochloride with chromatographic purity of more than 98.5%, concentrating the vancomycin hydrochloride to 150 mg/ml-250 mg/ml and freezing and drying after separating solvent by nanofiltration, to obtain a pure white vancomycin hydrochloride with a chromatographic purity of 99%.

BACKGROUND OF THE INVENTION

Vancomycin hydrochloride is an amphoteric glycopeptide antibiotic produced by fermentation of Actinomycetes *Amycolatopsis orienatalis* under controlling conditions, which has a molecular formula $C_{66}H_{75}C_{l2}N_9O_{24} \cdot HCl$ and a molecular weight of 1.486. Vancomycin hydrochloride acts by binding the C-terminal D-Ala-D-Ala peptides, which inhibits the synthesis of cell walls and also changes the permeability of cell membranes as well as synthesis of RNA. Vancomycin hydrochloride is particularly used for the initial treatment of serious or severe infections caused by staphylococci resistant to β-lactam antibiotics as well as in patients who are penicillin-sensitive or do not respond to penicillin or cephalosporine. It is reported by early literatures that vancomycin hydrochloride has serious kidney toxicity and ototoxicity and thus has not been widely used in clinical. However, due to a large number of uses of antibiotics recently, it would result in increasing clinical infections of methicillin-resistant *Staphylococcus aureus* (MASA), makes usages amount of vancomycin hydrochloride increased year by year. Therefore, it is very important to reduce toxicity of vancomycin hydrochloride and increase safety of usage of medicinal vancomycin hydrochloride, wherein improving the purity of medicinal vancomycin hydrochloride is an effective means. Recently, with continuous development of science and technology, persons skilled in the art constantly have improved purity of vancomycin hydrochloride, and severe kidney toxicity and ototoxicity caused by vancomycin hydrochloride are reduced constantly. Based on the above reasons, it is very important to develop a purification process of vancomycin hydrochloride with a higher purity, simple and feasible, and suitable for industrial production.

Vancomycin molecule is composed of two basic structures, including a saccharide group, α-o-vancosamine-β-o-glucosyl, and a heptapeptide backbone. The structure of vancomycin determines its instability, and vancomycin molecules is degraded to produce degradation products under the condition of acid, alkali or high temperature. In the meanwhile, multiple free phenolic hydroxyl groups of the structure are easily oxidized to quinoid. It has been reported by literatures that vancomycin would be hydrolyzed under the conditions of acid and high temperature to produce desvancosaminyl vancomycin or aglucovancomycin, by taking off one or two glycosyl, and degraded into amino vancomycin by taking off acylamino having two isomers under weak acidic condition. Based on these features of chemical structure of vancomycin, it is difficult to produce vancomycin hydrochloride with high purity It has been decades histories for developing products of vancomycin hydrochloride. In early preparation technology, vancomycin hydrochloride is prepared by crystallization using solvents such as methanol, ethanol, isopropanol and acetone etc. and precipitation using ammonium chloride or sodium chloride. However the purity is generally not high due to many impurities especially many structural analogues of vancomycin in the vancomycin fermentation medium. So it is difficult to meet the European Pharmacopoeia Standards with chromatographic purity of more than 93%.

The technology has been widely used in the separation and purification of vancomycin hydrochloride recently, with development of chromatographic separation technology of all kinds of medium. CN200710187300.5 performs chromatography using ion-exchange fillers such as glucan gel SEPHADEX® CM-25, agarose SP SEPHAROSE® or agarose CM SEPHAROSE®, wherein a mobile phase is ammonium bicarbonate of 4-6%, to obtain vancomycin hydrochloride with a chromatographic purity of 95%~98%, and then salting-out precipitate by adding sodium chloride solution, and afterwards separate and, wash by ethanol and dry to obtain vancomycin hydrochloride. The purity of vancomycin hydrochloride obtained by the method is higher, however the recovery rate is not high. Besides, this ion exchange chromatography method is not very ideal for removing pigment. So the product produced by the method is not very ideal in color appearance and solution absorbance.

PCT Patent Application No. WO2006061166 uses a reverse phase silica gel (octadecyl silica gel) with a, particle size of 5 μm as chromatographic medium, a mobile phase including an aqueous solution of 5 mM of ammonium acetate and 3% of methanol solution with pH=4.0, 2% of an analytical agent with n-pentanol in the mobile phase, to collect vancomyin hydrochloride with a chromatographic purity of more than 97.5%. Afterwards, the vancomyin hydrochloride is concentrated under vacuum to a concentration of 140 mg/ml, and the add methanol, then adjust pH=8.5 to 9.0 with an aqueous solution of ammonia, and cool to 0° C. to produce precipitate, and then separate and wash with methanol, and then dissolve the separation with water and adjust pH=3.2 and crystallize with isopropanol, and dry in vacuum, to obtain vancomycin hydrochloride with a purity of 97-99.3%. There are some deficiencies in the method of the patent, especially it is difficult for commercial expansive production. First of all, the metod uses different solvents as a mobile phase and an eluate, so it is difficult to recover solvents; Secondly, it can not reach a chromatographic purity of 99% for one-time due to reverse phase purification in the method. So it needs two steps in solvent crystallization, finally to obtain vancomyin hydrochloride under vacuum drying. However residual solvents can't be effectively removed in the solvent crystallization, and residual solvents can't meet the requirements of ICH. Finally, the product yield is not ideal in this method because of many steps.

Therefore, it may be seen from current literatures that no method of preparing vancomycin hydrochloride with high purity (chromatographic purity of more than 99%) is suitable for commercial production due to many deficiencies. In view of medication safety of vancomycin hydrochloride, methods for preparing vancomycin hydrochloride with high purity are needed.

SUMMARY OF INVENTION

The present invention provides a separation and purification method for vancomycin hydrochloride with high purity (chromatographic purity of more than 99%), low impurities and high efficiency suitable for commercial production. The method comprises the following steps: (1) obtaining a vancomycin hydrochloride solution from a crude vancomycin product by ion exchange chromatography and obtaining a first vancomycin hydrochloride concentrate by nanofiltration desalination and concentration; (2) adjusting the first vancomycin hydrochloride concentrate with a hydrochloric acid solution to pH=3.5-4.5, and then performing a column chromatography using a reverse chromatography column for the first vancomycin hydrochloride concentrate adjusted, wherein a stationary phase is C18 silica gel or polystyrene, and a mobile phase is methanol aqueous solution or ethanol aqueous solution containing ammonium salt; (3) collecting a chromatographic solution of content of vancomycin B of more than 98.5%; (4) adjusting the chromatographic solution with hydrochloric acid to pH=2.5-3.5, and separating solvent and salt by nanofiltration desalination and concentration to obtain a second vancomycin hydrochloride concentrate; and (5) obtaining a vancomycin dry powder with a chromatographic purity of up to 99% and a pure white appearance by dehydrating and drying the second vancomycin hydrochloride concentrate of step (4).

Preferably, the vancomycin hydrochloride solution of step (1) obtained by ion exchange chromatography has a chromatographic purity of more than 95%. The vancomycin hydrochloride solution with a chromatographic purity of not lower than 95% is produced by the following method of the prior art. (1) firstly, according to the method of the Chinese patent publication No. CN01132048.6, *Amycolatopsis Orientalis* SIPI43491 as fermentation strains is inoculated to a first seeding tank by culturing an inoculum, and cultured in a fermentation tank after expanding culture in a second seeding tank at, a control temperature of 24~34□, and a culture pressure of 0.01~0.08 MPa, under controlling a dissolved oxygen and pH in the process, with a fermentation period of 4~6 days, to obtain a vancomycin fermentation broth. (2) secondly, according to method of the Chinese patent application No. CN200710198599.4, the vancomycin fermentation broth is extracted by macroporous adsorptive resin, eluted by an acidic aqueous solution containing ethanol, decolorized by adding an activated carbon into the eluent to obtain a destained solution, and then ammonium bicarbonate is added into the destained solution, and adjusted to pH=7.5~8.5 with ammonia hydroxide, then stirred and standed to obtain a crude vancomycin product with a chromatographic purity of not lower than 80% (the crude vancomycin product is referred to as the crude vancomycin product of step (1). (3) The crude vancomycin product is dissolved in a purified water and is filtered by a ceramic membrane with a pore diameter of 0.01~0.5 μm, to obtain a clear vancomycin filtrate. And the clear vancomycin filtrate is purified by an ion exchange chromatography column to obtain an effective chromatographic solution with a content of vancomycin B of more than 95% (i.e., the chromatographic purity of vancomycin is not lower than 95% of vancomycin hydrochloride solution). The filler of the ion exchange chromatography column is a cation exchange SEPHADEX® or SEPHAROSE®. The vancomycin filtrate is applied for column chromatography under an acidic condition, and is applied for chromatography under an alkali metal salt or ammonium salt condition, wherein $NH_4^+$ salts and $Na^+$ salts may be NaCl, $NH_4HCO_3$ and $(NH_4)_2CO_3$, etc.; the fractions with a content of vancomycin B of more than 93% are collected when chromatography is performed. It makes the content of vancomycin B of more than 95% in the effective chromatographic solution.

The effective chromatographic solution containing vancomycin with a chromatographic purity of not lower than 95% is performed by nanofiltration to obtain a concentrate containing vancomycin hydrochloride of 10-20% (that is, the concentration is 100 mg/ml-200 mg/ml), and preferably the concentrate is stored at a temperature of 2-8□. The nanofiltration membrane with a molecular weight of 100-800 Da is used for nanofiltration. Wherein, the concentrated temperature is equal to or lower than 20□.

The concentrate is adjusted to pH=3.5~4.5 with 4N hydrochloric acid solution and is passed through a reverse chromatographic column with preferably C18 silica gel or reverse polymer as filler, and the particle size of silica gel is preferably 5 μm-60 μm, the particle size of polymer such as polystyrene is preferably 20 μm-40 μm. The mobile phase is methanol or ethanol, and the buffer agent is ammonium salt to adjust pH, preferably to adjust to pH=3.5~5.5 with hydrochloric acid or acetic acid, preferably perform a gradient elution with ammonium chloride and ammonium acetate, wherein, the concentration of methanol aqueous solution or ethanol aqueous solution containing ammonium salt is 0.1 wt % to 1 wt %. The fractions with a content of vancomycin B of more than 98.5% are collected, to make the content of vancomycin B of more than 99% in the mixed eluent.

The mixed eluate is adjusted to pH=2.5~3.5 with 4N hydrochloric acid, and then separate solvents and salts by nanofiltration, preferably, the nanofiltration is performed by using nanofiltration membrane with a molecular weight of 100-800 Da. Wherein, the concentrated temperature is equal to or lower than 20° C. The solution is concentrated to obtain a concentrate containing vancomycin hydrochloride of 15-25%, and the concentrate is dehydrated by using a freeze dryer or spray drier (wherein the method of dehydration is freeze drying, spray drying, salting-out crystallization or solvent crystallization, the method of dehydration belongs to regular prior arts) and dried to obtain vancomycin hydrochloride with a chromatographic purity of more than 99%. The absorbance of vancomycin hydrochloride powder is less than 0.02, and the whiteness of vancomycin hydrochloride powder is more than 88% under the concentration of 10% and wavelength of 450 nm.

In comparison with previous patents, the preparation method of the present invention has the following advantages: the purity of final vancomycin hydrochloride is more than 99% and its color appearance has been greatly improved by ion exchange chromatography and reverse silica gel chromatography; the content of vancomycin is more than 99% by two chromatography of ion exchange chromatography and reverse chromatography; and the method is simple and easy; using ammonium salt and ethanol or methanol as mobile phase of reverse chromatography. It is easier to subsequently process and solvent recovery in comparison with previous patents; and the eluent is easily concentrated by nanofiltration membrane, and the operation is convenient. So the process not only improves quality of products, but also is suitable for expanding commercial production.

DETAILED DESCRIPTION OF THE PRESENT INVENTION AND PREFERRED EMBODIMENTS THEREOF

Hereafter, the present invention will be further illustrated with reference to examples. The examples are given only for illustration of the technical solution of the present invention and should not be construed to limit the present invention.

The present invention is further specifically illustrated by the following examples, but is not limited to the following examples and the extent of process parameters of examples.

Example 1: Preparation of Vancomycin Hydrochloride Solution with a Content of Vancomycin B of not Lower than 95%

Figure 1:
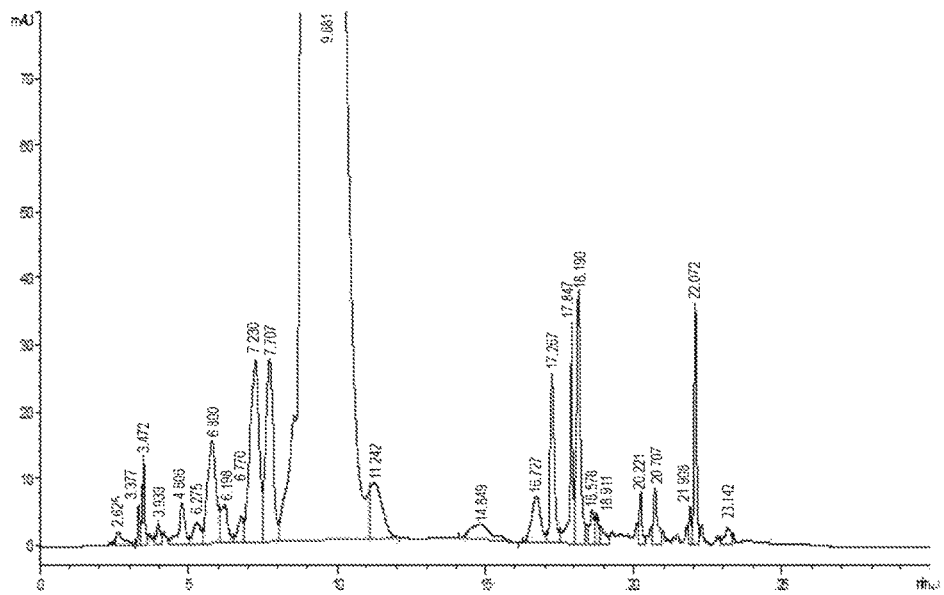
FIG. 1 shows chromatogram of crude vancomycin of example 1, the content of vancomycin B is 90.2%.

250 g of crude vancomycin is dissolved to 2.0 L purified water in a beaker, and stirred fully, and filtered with a filter membrane of pore size of 0.2 μm after being completely dissolved, and then diluted by water, to finally obtain 3.0 L of the dissolved solution containing crude vancomycin hydrochloride with the concentration of 43.6 mg/ml and chromatographic purity of 90.2%, as shown in FIG. 1.

Figure 2:
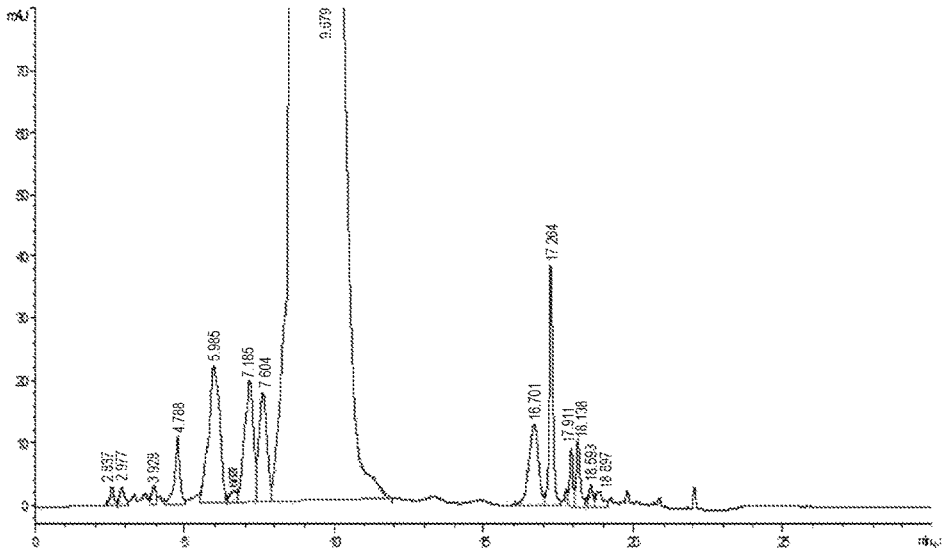
FIG. 2 shows chromatogram of vancomycin hydrochloride concentrate of example 1, the content of vancomycin B is 95.3%.

3000 ml of the dissolved solution of crude vancomycin hydrochloride is applied to a 8 cm*60 cm glass chromatographic column containing glucan SEPHADEX® CM-25, the capacity of the column is 4% of the chromatographic column volume. The column solution is mixed with ⅕ of chromatographic filler to form a mixed solution, and then the mixed solution is directly applied to the glass chromatographic column, and then is washed by a purified water at a flow rate of 1.5 times column volumes per hour, after washing 6 times column volumes, and is prewashed by 0.3% (w/v) $NH_4HCO_3$ aqueous solution with one times column volume per hour. the prewashing volume is 15~20 times column volumes. After finishing prewashing, the content of vancomycin B of the eluent is more than 90%, and then eluted by 5% (w/v) $NH_4HCO_3$ aqueous solution to obtain vancomycin, and the eluent is collected in fractions, and the fractions with the content of vancomycin B of more than 95% determined by HPLC are mixed, and then adjusted to pH=3.1 with 4N hydrochloric acid, to obtain an effective eluent of 5600 ml with the concentration of 18.6 mg/ml, a chromatographic purity of 96.5%, as shown in FIG. 2.

Afterwards the effective eluent is desalted and concentrated by nanofiltration membrane with pore diameter of molecular weight of 400, the purified water is added for 5 times, to finally obtain a dialysate with the conductivity of 1255 μs/cm, and then the feed liquid is concentrated to obtain vancomycin hydrochloride concentrate with the concentration of 156 mg/ml, pH=3.8, the chromatographic purity of 95.3% (refer to FIG. 2), the volume of 680 ml, and the concentrate is stored at 2-8° C. for use.

Example 2: Preparation of Vancomycin Hydrochloride with High Purity 680 ml of the concentrate of example 1 is passed through a column (15 cm*30 cm) having C18 silica gel filler with particle size of 30 μm, adjusted to pH 4.0 by hydrochloric acid, pre-washed for 100 mim with an aqueous solution containing $NH_4Cl$ of 0.2% (W/V) and methanol aqueous solution of 8% (V/V) as a mobile phase at the flow rate of 5 BV/h, and then the methanol proportion of the mobile phase is increased to 12% to elute at the flow rate of 5 BV/h. At the on-line detection wavelength $\lambda=280$, the eluent is collected about 10 bottles with 2.5 L per bottle when the absorption value begins rising rapidly, and the content of vancomycin B per bottle is determined, then the eluents with a chromatographic purity of more than 98.5% are mixed to obtain the mixed chromatographic solution of 12.5 L, with the concentration of 6.8 mg/ml, and the mixed chromatographic solution is adjusted to pH=2.8 with 4N hydrochloric acid.

Figure 3:
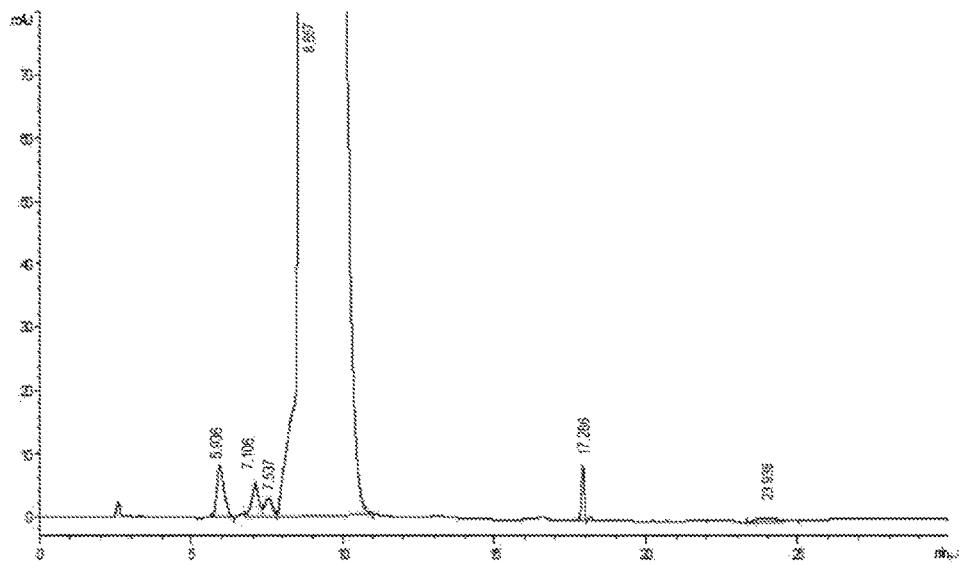
FIG. 3 shows chromatogram of the product of vancomycin hydrochloride of example 2, the content of vancomycin B is 99.1%.

The above chromatographic solution is passed through a nanofiltration membrane with the pore diameter of molecular weight of 400 for desolvation, when no solvent is produced anymore, the mixture solution is concentrated to a concentrate with concentration of 240 mg/ml and volume of 338 ml, and then the concentrate is filtered by filter membrane of 0.45 μm and is freeze-dried in the freeze dryer to obtain freeze-dried powders of vancomycin hydrochloride of 68.5 g, with the yield of 64.6%, chromatographic purity of 99.1% (refer to FIG. 3), and the absorbance of solution of 10% at 450 nm is 0.012.

Example 3: Comparison of Concentration Effects by Nanofiltration Membrane with Different Pore Diameter Nanofiltration membrane tubes with different pore diameter such as 100 Da, 200 Da, 400 Da and 800 Da and with the same filter area of 0.32 $m^2$ are selected respectively, to install in turn on a small nanofiltration membrane equipment for lab (type LNG-NF-101). 8000 ml of concentrate containing 10% vancomycin hydrochloride is divided into 4 portions, and one of them is concentrated by nanofiltration, with the pressure of 10 bar controlled by circulating pump. Potency of the dialysis sample is detected at the beginning of the concentration, and record the flow rate of dialysis, when the circulating fluid is concentrated to volume of 1000 ml, the potency detection of dialysis sample is finished, and the flow rate of dislysis is recorded. The equipment is washed after using per time, and the nanofiltration membrane tube is replaced by next one, use another concentrate for experiment. The assay results are shown as follows:

| Testing item | Pore diameter | | | |
|---|---|---|---|---|
| | 100 Da | 200 Da | 400 Da | 800 Da |
| Initiate flow rate (L/H) | 2.2 | 4 | 4.2 | 4.2 |
| Initiate potency (μ/ml) | 5 | 6 | 5 | 8 |
| End flow rate (L/H) | 1.6 | 3.8 | 3.8 | 4.0 |
| End potency (μ/ml) | 6 | 7 | 7 | 8 |

As shown in above Table, nanofiltration membranes with different pore diameter have little impact on potency of dialysate. So all of them are suitable for concentrating vancomycin hydrochloride. But membrane tubes with different pore diameters have effects on flow rates, and the membrane tubes with pore diameters of greater than 200 Da is more appropriate to the flow rate.

Figure 4:
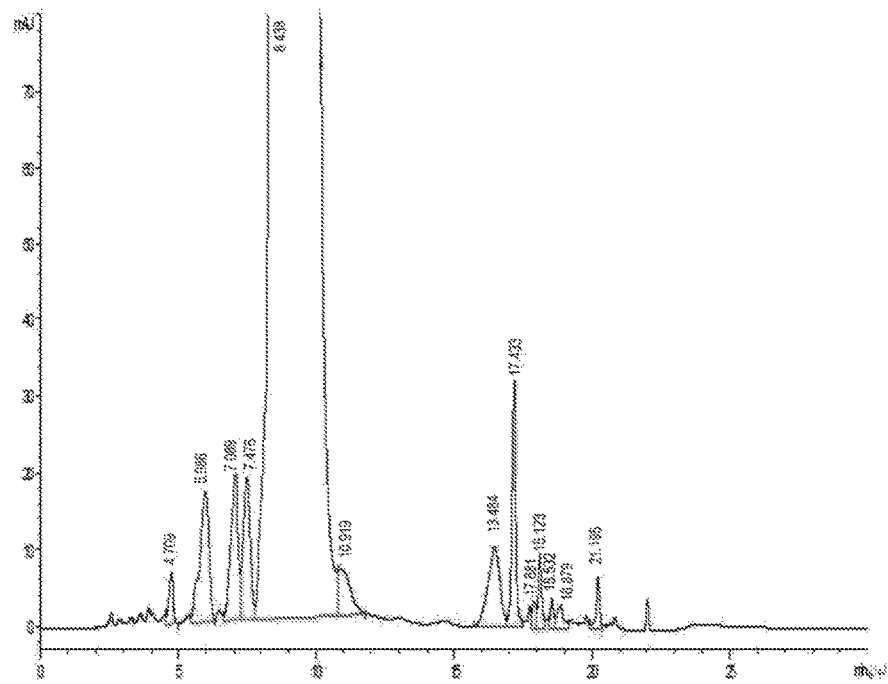
FIG. 4 shows chromatogram of vancomycin hydrochloride concentrate of examples 4-6, the content of vancomycin B is 95.8%.

Example 4: Comparison of C18 Silica Gels with Different Particle Sizes 330 ml of the concentrate with the concentration of 150 mg/ml, chromatographic purity of 95.8% (refer to FIG. 4) is adjusted to pH=4.0 with hydrochloric acid or sodium hydroxide solution, is filled into a preparative column (15 cm*30 cm) containing C18 silica gel filler with the particle size of 5 μm and is adjusted to pH=4.0 with hydrochloric acid, and pre-washed for 100 min with an aqueous solution containing 0.1% NH$_4$Cl(W/V) and 8% (V/V) methanol aqueous solution as mobile phase, at the flow rate of 5 BV/h, then the proportion of methanol in the mobile phase is increased to 12% to elute at the flow rate of 5 BV/h. the on-line detection wavelength λ=280, the eluent is collected when the absorptive value begins with rising rapidly, to totally collect 8 bottles, one bottle per 2.5 L, and to determine the content of vancomycin B per bottle, and then the eluents with a chromatographic purity of more than 98.5% are mixed to obtain a mixed chromatographic solution of 10 L, with the concentration of 3.8 mg/ml, and the mixed chromatographic solution is adjusted to pH=2.8 with 4N hydrochloric acid.

Figure 5:
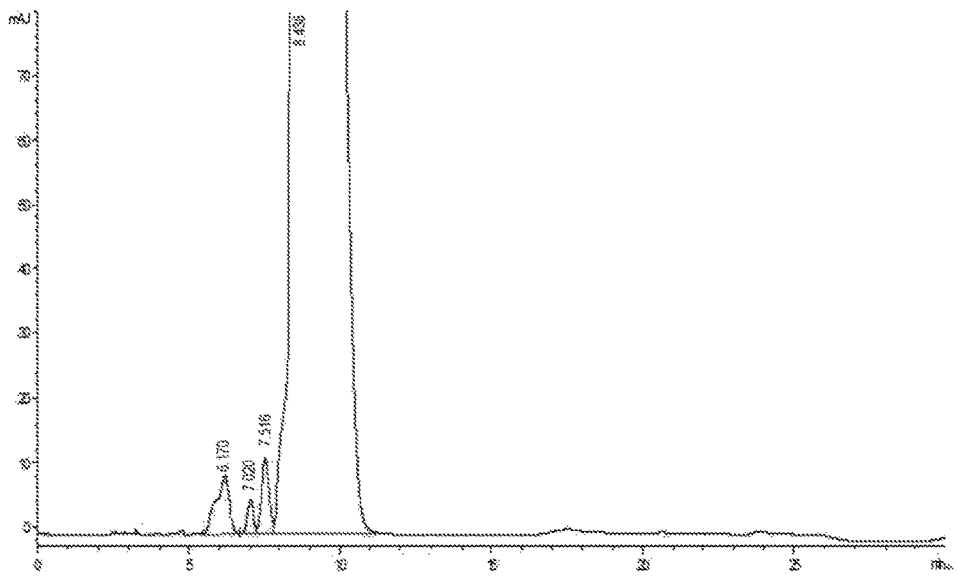
FIG. 5 shows chromatogram of the product of vancomycin hydrochloride of example 4, the content of vancomycin B is 99.0%.

The above chromatographic solution is passed through a nanofiltration membrane with a pore diameter of molecular weight of 400 for desolvation. the mixture solution is concentrated to a concentration of 150 mg/ml and volume of 248 ml when no solvent is produced anymore, and then the concentrate is filtered by a filter membrane of 0.45 μm, and is freeze-dried in a freeze dryer to obtain freeze-dried powders of vancomycin hydrochloride of 30.8 g, with the yield of 62.2%, the chromatographic purity of 99.0% (refer to FIG. 5), and the absorbance A of solution of 10% at 450 nm is 0.014.

Example 5: Comparison of C18 Silica Gels with Different Particle Sizes 330 ml of the concentrate with the concentration of 150 mg/ml, chromatographic purity of 95.8% (refer to FIG. 4) is adjusted to pH=4.0 with hydrochloric acid or sodium hydroxide solution, is filled into a preparative column (15 cm*30 cm) containing C18 silica gel filler with particle size of 30 μm and is adjusted to pH=4.0 with hydrochloric acid, and pre-washed for 100 min with an aqueous solution containing 0.1% NH$_4$Cl(W/V) and 8% (V/V) methanol aqueous solution as mobile phase, at the flow rate of 5 BV/h, then the proportion of methanol in the mobile phase is increased to 12% to elute at the flow rate of 5 BV/h. the on-line detection wavelength λ=280, the eluent is collected when the absorptive value begins with rising rapidly, to totally collect 8 bottles, one bottle per 2.5 L, and to determine the content of vancomycin B per bottle, and then the eluents with a chromatographic purity of more than 98.5% are mixed to obtain a mixed chromatographic solution of 10 L, with the concentration of 4.1 mg/ml, and the mixed chromatographic solution is adjusted to pH=2.8 with 4N hydrochloric acid.

Figure 6:
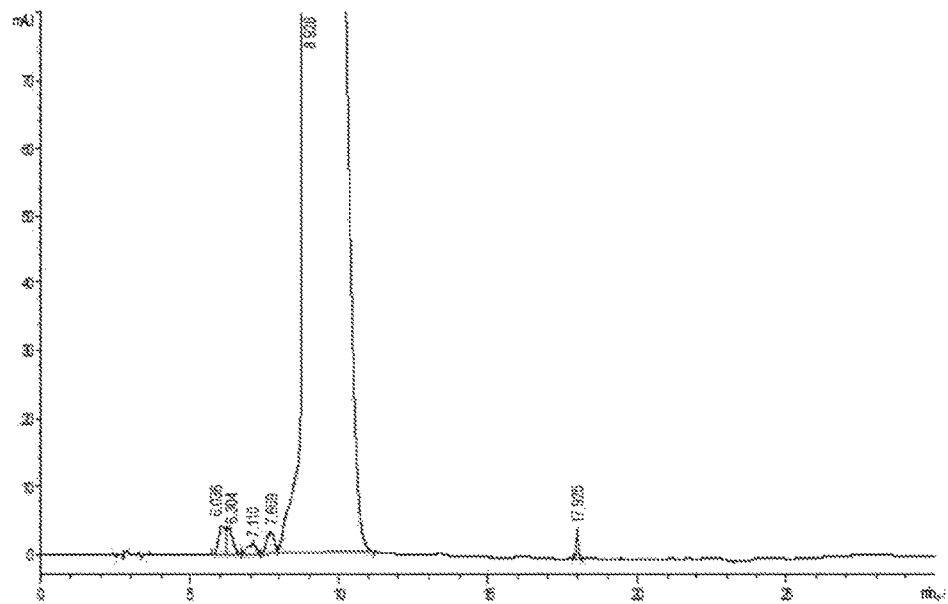
FIG. 6 shows chromatogram of the product of vancomycin hydrochloride of example 5, the content of vancomycin B is 99.2%.

The above chromatographic solution is passed through a nanofiltration membrane with a pore diameter of molecular weight of 400 for desolvation. the mixture solution is concentrated to a concentration of 150 mg/ml and volume of 265 ml when no solvent is produced anymore, and then the concentrate is filtered by a filter membrane of 0.45 μm, and is freeze-dried in a freeze dryer to obtain freeze-dried powders of vancomycin hydrochloride of 32.5 g, with the yield of 65.6%, the chromatographic purity of 99.2% (refer to FIG. 6), and the absorbance A of solution of 10% at 450 nm is 0.015.

Example 6: Comparison of C18 Silica Gels with Different Particle Sizes 330 ml of the concentrate with the concentration of 150 mg/ml, chromatographic purity of 95.8% is adjusted to pH=4.0 with hydrochloric acid or sodium hydroxide solution, is filled into a preparative column (15 cm*30 cm) containing C18 silica gel filler with particle size of 60 μm and is adjusted to pH=4.0 with hydrochloric acid, and pre-washed for 100 min with an aqueous solution containing 0.1% NH$_4$Cl(W/V) and 8% (V/V) methanol aqueous solution as mobile phase, at the flow rate of 5 BV/h, then the proportion of methanol in the mobile phase is increased to 12% to elute at the flow rate of 5 BV/h. the on-line detection wavelength λ=280, the eluent is collected when the absorptive value begins with rising rapidly, to totally collect 8 bottles, one bottle per 2.5 L, and to determine the content of vancomycin B per bottle, and then the eluents with a chromatographic purity of more than 98.5% are mixed to obtain a mixed chromatographic solution of 10 L, with the concentration of 3.8 mg/ml mg/ml, and the mixed chromatographic solution is adjusted to pH=2.8 with 4N hydrochloric acid.

Figure 7:
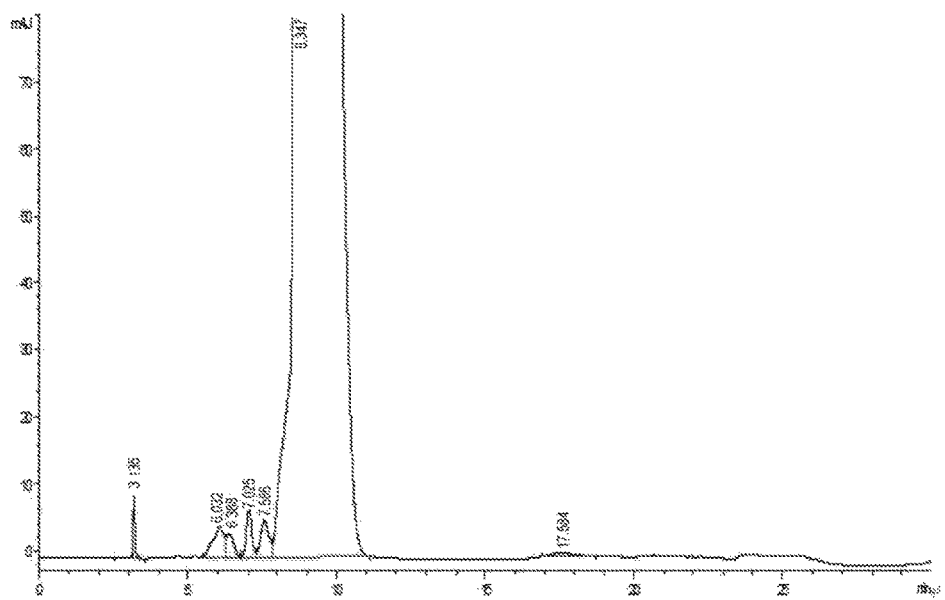
FIG. 7 shows chromatogram of the product of vancomycin hydrochloride of example 6, the content of vancomycin B is 99.0%.

The above chromatographic solution is passed through a nanofiltration membrane with a pore diameter of molecular weight of 400 for desolvation. the mixture solution is concentrated to a concentration of 150 mg/ml and volume of 245 ml when no solvent is produced anymore, and then the concentrate is filtered by a filter membrane of 0.45 μm, and is freeze-dried in a freeze dryer to obtain freeze-dried powders of vancomycin hydrochloride of 29.8 g, with the yield of 60.2%, the chromatographic purity of 99.0% (refer to FIG. 7), and the absorbance A of solution of 10% at 450 nm is 0.012.

It can be found from comparison of examples 4, 5 and 6 that the reverse chromatography containing C18 silica gel filler with different particle size has little impact on the chromatographic purity, yield and absorbance. But, as for operating pressures, the smaller the particle size is, the greater the pressure is. So it is most suitable for mass production to choose C18 silica gel with particle size of 30 μm-60 μm.

Figure 8:
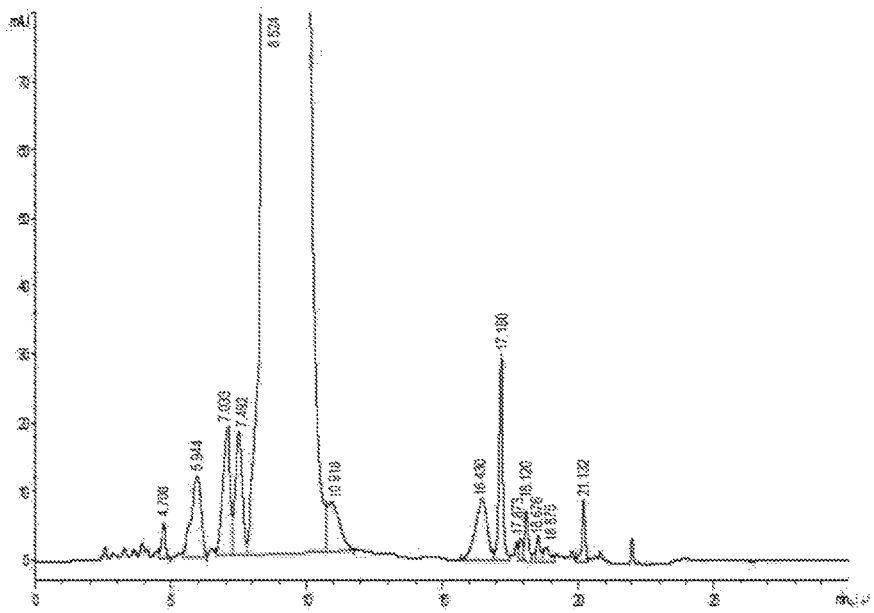
FIG. 8 shows chromatogram of the vancomycin hydrochloride concentrate of examples 7-9, the content of vancomycin B is 95.9%.

Example 7: Comparison of $CH_3COONH_4$ and $NH_4Cl$ in the Mobile Phase 330 ml of the concentrate with the concentration of 152 mg/ml, chromatographic purity of 95.9% (refer to FIG. 8) is adjusted to pH=4.0 with hydrochloric acid or sodium hydroxide solution, is filled into a preparative column (15 cm*30 cm) containing C18 silica gel filler with particle size of 30 μm and is adjusted to pH=4.0 with acetic acid, and pre-washed for 100 min with an aqueous solution containing 0.1% $CH_3COONH_4$ (W/V) and 8% (V/V) methanol aqueous solution as mobile phase, at the flow rate of 5 BV/h, then the proportion of methanol in the mobile phase is increased to 12% to elute at the flow rate of 5 BV/h. the on-line detection wavelength λ=280, the eluent is collected when the absorptive value begins with rising rapidly, to totally collect 8 bottles, one bottle per 2.5 L, and to determine the content of vancomycin B per bottle, and then the eluents with a chromatographic purity of more than 98.5% are mixed to obtain a mixed chromatographic solution of 10 L, with the concentration of 4.0 mg/ml, and the mixed chromatographic solution is adjusted to pH=2.8 with 4N hydrochloric acid.

Figure 9:
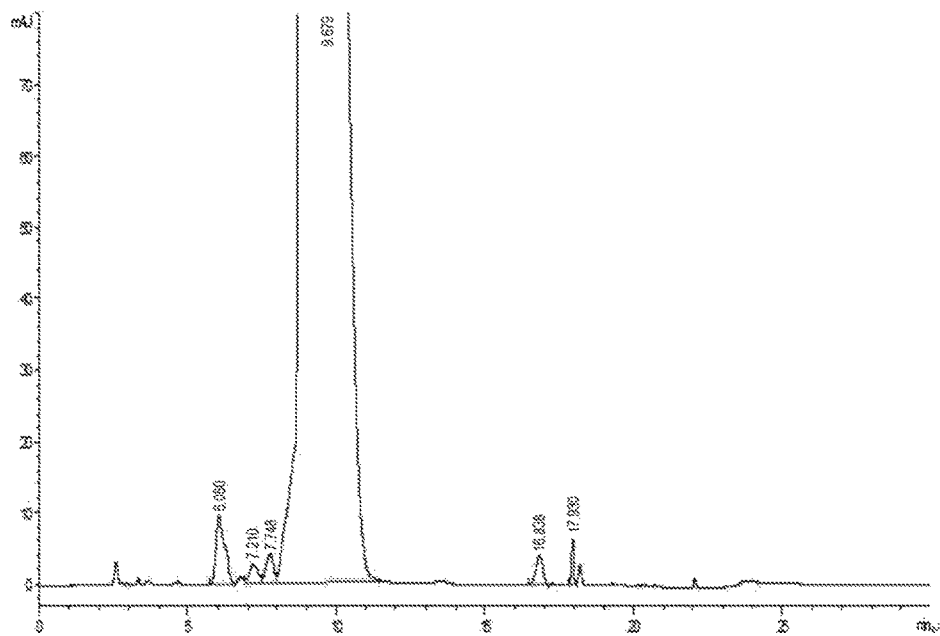
FIG. 9 shows chromatogram of the product of vancomycin hydrochloride of example 7, the content of vancomycin B is 99.0%.

The above chromatographic solution is passed through a nanofiltration membrane with a pore diameter of molecular weight of 400 for desolvation. the mixture solution is concentrated to a concentration of 150 mg/ml and volume of 252 ml when no solvent is produced anymore, and then the concentrate is filtered by a filter membrane of 0.45 μm, and is freeze-dried in a freeze dryer to obtain freeze-dried powders of vancomycin hydrochloride of 31.1 g, the chromatographic purity of 99.0% (refer to FIG. 9), and the absorbance A of solution of 10% at 450 nm is 0.017.

It can be found from comparison of example 5 that the components of the mobile phase containing NH4Cl and its yields is little difference from that of CH3COONH4.

Example 8: Comparison of Different Proportions of $NH_4Cl$ in Mobile Phase 330 ml of the concentrate with the concentration of 152 mg/ml, chromatographic purity of 95.9% is adjusted to pH=4.0 with hydrochloric acid solution, is filled into a preparative column (15 cm*30 cm) containing C18 silica gel filler with particle size of 30 μm and is adjusted to pH=4.0 with hydrochloric acid, and pre-washed for 100 min with an aqueous solution containing 0.5% $NH_4Cl$ (W/V) and 8% (V/V) methanol aqueous solution as mobile phase, at the flow rate of 5 BV/h, then the proportion of methanol in the mobile phase is increased to 12% to elute at the flow rate of 5 BV/h. the on-line detection wavelength λ=280, the eluent is collected when the absorptive value begins with rising rapidly, to totally collect 9 bottles, one bottle per 2.5 L, and to determine the content of vancomycin B per bottle, and then the eluents with a chromatographic purity of more than 98.5% are mixed to obtain a mixed chromatographic solution of 12.5 L, with the concentration of 3.2 mg/ml, and the mixed chromatographic solution is adjusted to pH=2.8 with 4N hydrochloric acid.

Figure 10:
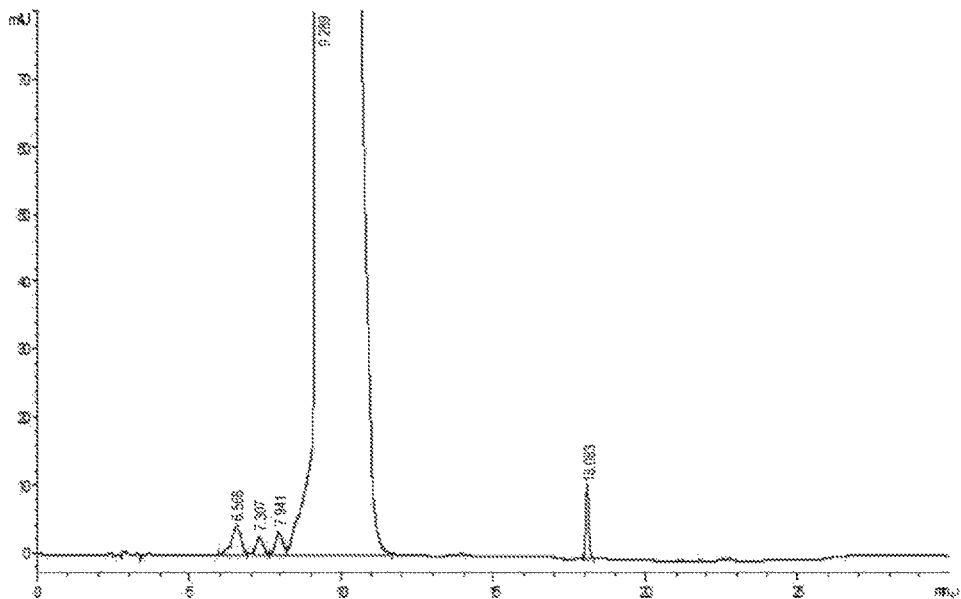
FIG. 10 shows chromatogram of the product of vancomycin hydrochloride of example 8, the content of vancomycin B is 99.2%.
Figure 11:
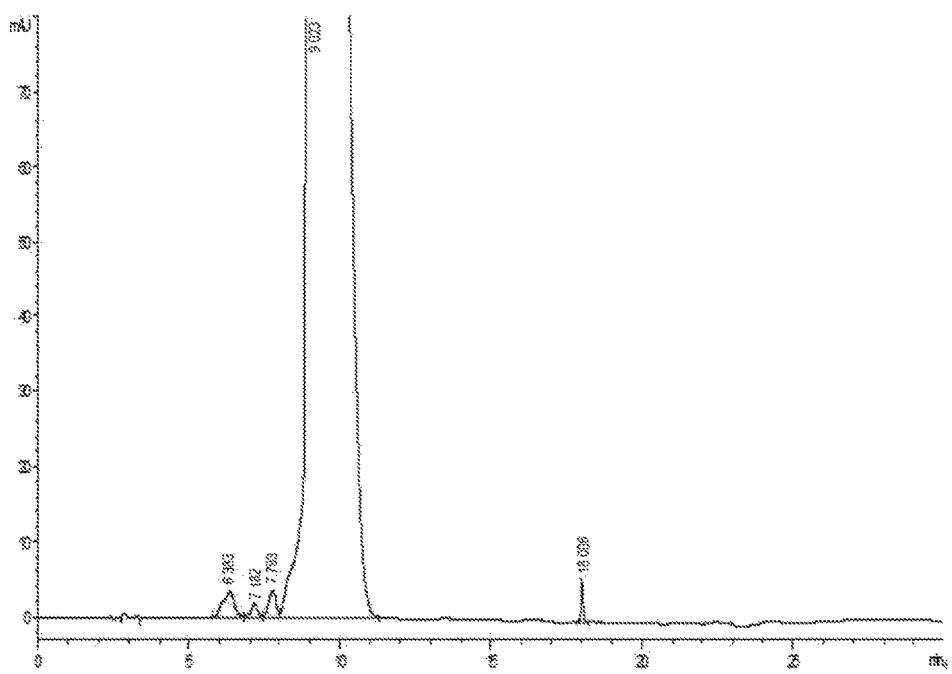
FIG. 11 shows chromatogram of the product of vancomycin hydrochloride of example 9, the content of vancomycin B is 99.3%.

The above chromatographic solution is passed through a nanofiltration membrane with a pore diameter of molecular weight of 400 for desolvation. the mixture solution is concentrated to a concentration of 150 mg/ml and volume of 260 ml when no solvent is produced anymore, and then the concentrate is filtered by a filter membrane of 0.45 μm, and is freeze-dried in a freeze dryer to obtain freeze-dried powders of vancomycin hydrochloride of 32.1 g, the yield of 64.0%, the chromatographic purity of 99.2% (refer to FIG. 10), and the absorbance A of solution of 10% at 450 nm is 0.016.

Example 9: Comparison of Different Proportions of $NH_4Cl$ in Mobile Phase 330 ml of the concentrate with the concentration of 152 mg/ml, chromatographic purity of 95.9% is adjusted to pH=4.0 with hydrochloric acid solution, is filled into a preparative column (15 cm*30 cm) containing C18 silica gel filler with particle size of 30 μm and is adjusted to pH=4.0 with hydrochloric acid, and pre-washed for 100 min with an aqueous solution containing 1.0% $NH_4Cl$ (W/V) and 8% (V/V) methanol aqueous solution as mobile phase, at the flow rate of 5 BV/h, then the proportion of methanol in the mobile phase is increased to 12% to elute at the flow rate of 5 BV/h. the on-line detection wavelength λ=280, the eluent is collected when the absorptive value begins with rising rapidly, to totally collect 9 bottles, one bottle per 2.5 L, and to determine the content of vancomycin B per bottle, and then the eluents with a chromatographic purity of more than 98.5% are mixed to obtain a mixed chromatographic solution of 12.5 L, with the concentration of 3.1 mg/ml, and the mixed chromatographic solution is adjusted to pH=2.8 with 4N hydrochloric acid.

The above chromatographic solution is passed through a nanofiltration membrane with a pore diameter of molecular weight of 400 for desolvation. the mixture solution is concentrated to a concentration of 150 mg/ml and volume of 258 ml when no solvent is produced anymore, and then the concentrate is filtered by a filter membrane of 0.45 μm, and is freeze-dried in a freeze dryer to obtain freeze-dried powders of vancomycin hydrochloride of 32.0 g, the yield of 63.8%, the chromatographic purity of 99.3% (refer to FIG. 10), and the absorbance A of solution of 10% at 450 nm is 0.014.

It can be found from comparison of examples 5, 8 and 9 that the aqueous solution containing different contents of $NH_4Cl$ (W/V) and 8% (V/V) methanol aqueous solution as the mobile phases has little impact on the yields, chromatographic components and absorbancy, but has impacts on the volume collected.

Example 10: Comparison of Different pH of the Column Solution and the Mobile Phase 670 ml of the concentrate with the concentration of 146 mg/ml, chromatographic purity of 96.4% is adjusted to pH=3.5 with hydrochloric acid solution, is filled into a preparative column (15 cm*30 cm) containing C18 silica gel filler with particle size of 30 μm and is adjusted to pH=3.5 with hydrochloric acid, and pre-washed for 100 min with an aqueous solution containing 0.5% $NH_4Cl$ (W/V) and 8% (V/V) methanol aqueous solution as mobile phase, at the flow rate of 5 BV/h, then the proportion of methanol in the mobile phase is increased to 12% to elute at the flow rate of 5 BV/h, the on-line detection wavelength λ=280, the eluent is collected when the absorptive value begins with rising rapidly, to totally collect 10 bottles, one bottle per 2.5 L, and to determine the content of vancomycin B per bottle, and then the eluent with the chromatographic purity of more than 98.5% are mixed to obtain the mixed chromatographic solution of 12.5 L, with the concentration of 6.3 mg/ml, and the mixed chromatographic solution is adjusted to pH=2.8 with 4N hydrochloric acid.

The above chromatographic solution is passed through a nanofiltration membrane with a pore diameter of molecular weight of 400 for desolvation. the mixture solution is concentrated to a concentration of 200 mg/ml and volume of 380 ml when no solvent is produced anymore, and then the concentrate is filtered by a filter membrane of 0.45 μm, and is freeze-dried in a freeze dryer to obtain freeze-dried powders of vancomycin hydrochloride of 63.1 g, the yield of 64.5%, the chromatographic purity of 99.2%, and the absorbance A of solution of 10% at 450 nm is 0.015.

Example 11: Comparison of Different pH of the Column Solution and the Mobile Phase 670 ml of the concentrate with the concentration of 146 mg/ml, chromatographic purity of 96.4% is adjusted to pH=4.5 with hydrochloric acid solution, is filled into a preparative column (15 cm*30 cm) containing C18 silica gel filler with particle size of 30 μm and is adjusted to pH=4.5 with hydrochloric acid, and pre-washed for 100 min with an aqueous solution containing 0.5% $NH_4Cl$ (W/V) and 8% (V/V) methanol aqueous solution as mobile phase, at the flow rate of 5 BV/h, then a proportion of methanol in the mobile phase is increased to 12% to elute at the flow rate of 5 BV/h, the on-line detection wavelength λ=280, the eluent is collected when the absorptive value begins with rising rapidly, to totally collect 10 bottles, one bottle per 2.5 L, and to determine the content of vancomycin B per bottle, and then the eluent with the chromatographic purity of more than 98.5% are mixed to obtain the mixed chromatographic solution of 15 L, with the concentration of 5.1 mg/ml, and the mixed chromatographic solution is adjusted to pH=2.8 with 4N hydrochloric acid.

The above chromatographic solution is passed through a nanofiltration membrane with a pore diameter of molecular weight of 400 for desolvation. the mixture solution is concentrated to a concentration of 200 mg/ml and volume of 360 ml when no solvent is produced anymore, and then the concentrate is filtered by a filter membrane of 0.45 μm, and is freeze-dried in a freeze dryer to obtain freeze-dried powders of vancomycin hydrochloride of 58.2 g, the yield of 59.5%, the chromatographic purity of 99.0%, and the absorbance A of solution of 10% is 0.018.

It can be found from comparison of examples 7, 10 and 11 that pH=3.5 and pH=4.0 of the column solution and the mobile phase have little effect on the product yield and components, and pH=4.5 of the column solution would result in increasing of the collected volume, and the yield and components are affected slightly.

Example 12: Comparison of Different Concentration $CH_3COONH_4$ in the Mobile Phase 330 ml of the concentrate with the concentration of 154 mg/ml, chromatographic purity of 95.9% is adjusted to pH=4.0 with hydrochloric acid or sodium hydroxide, is filled into a preparative column (15 cm*30 cm) containing C18 silica gel filler with particle size of 30 μm and is adjusted to pH=4.0 with hydrochloric acid, and pre-washed for 100 min with an aqueous solution containing 0.5% $CH_3COONH_4$ (W/V) and 8% (V/V) methanol aqueous solution as mobile phase, at the flow rate of 5 BV/h, then the proportion of methanol in the mobile phase is increased to 12% to elute at the flow rate of 5 BV/h. the on-line detection wavelength λ=280, the eluent is collected when the absorptive value begins with rising rapidly, to totally collect 8 bottles, one bottle per 2.5 L, and to determine the content of vancomycin B per bottle, and then the eluents with a chromatographic purity of more than 98.5% are mixed to obtain a mixed chromatographic solution of 10 L, with the concentration of 4.1 mg/ml, and the mixed chromatographic solution is adjusted to pH=2.8 with 4N hydrochloric acid.

The above chromatographic solution is passed through a nanofiltration membrane with a pore diameter of molecular weight of 400 for desolvation. the mixture solution is concentrated to a concentration of 150 mg/ml and volume of 260 ml when no solvent is produced anymore, and then the concentrate is filtered by a filter membrane of 0.45 μm, and is freeze-dried in a freeze dryer to obtain freeze-dried powders of vancomycin hydrochloride of 32.5 g, the yield of 64.0%, the chromatographic purity of 99.1%, and the absorbance A of solution of 10% is 0.013.

Example 13: Comparison of Different Concentration $CH_3COONH_4$ in the Mobile Phase 330 ml of the concentrate with the concentration of 154 mg/ml is adjusted to pH=4.0 with hydrochloric acid or sodium hydroxide, is filled into a preparative column (15 cm*30 cm) containing C18 silica gel filler with particle size of 30 μm and is adjusted to pH=4.0 with hydrochloric acid, and pre-washed for 100 min with an aqueous solution containing 1% $CH_3COONH_4$ (W/V) and 8% (V/V) methanol aqueous solution as mobile phase, at the flow rate of 5 BV/h, then the proportion of methanol in the mobile phase is increased to 12% to elute at the flow rate of 5 BV/h. the on-line detection wavelength λ=280, the eluent is collected when the absorptive value begins with rising rapidly, to totally collect 9 bottles, one bottle per 2.5 L, and to determine the content of vancomycin B per bottle, and then the eluents with a chromatographic purity of more than 98.5% are mixed to obtain a mixed chromatographic solution of 12.5 L, with the concentration of 3.2 mg/ml, and the mixed chromatographic solution is adjusted to pH=2.8 with 4N hydrochloric acid.

The above chromatographic solution is passed through a nanofiltration membrane with a pore diameter of molecular weight of 400 for desolvation. the mixture solution is concentrated to a concentration of 150 mg/ml and volume of 265 ml when no solvent is produced anymore, and then the concentrate is filtered by a filter membrane of 0.45 μm, and is freeze-dried in a freeze dryer to obtain freeze-dried powders of vancomycin hydrochloride of 33.0 g, the yield of 65.0%, the chromatographic purity of 99.0%, and the absorbance A of solution of 10% is 0.015.

It can be found from comparison of examples 7, 12 and 13 that the aqueous solution containing different concentration $CH_3COONH_4$ (W/V) and 8% (V/V) methanol aqueous solution as the mobile phase has little impact on the product component, yield and absorbancy, however high concentration $CH_3COONH_4$ has impact on the collected volume.

Example 14: Comparison of Different pH in $CH_3COONH_4$ System as Mobile Phase 670 ml of the concentrate with the concentration of 145 mg/ml, chromatographic purity of 96.6% is adjusted to pH=3.5 with hydrochloric acid or sodium hydroxide, is filled into a preparative column (15 cm*30 cm) containing C18 silica gel filler with particle size of 30 μm and is adjusted to pH=3.5 with hydrochloric acid, and pre-washed for 100 min with an aqueous solution containing 0.5% $CH_3COONH_4$ (W/V) and 8% (V/V) methanol aqueous solution as mobile phase, at the flow rate of 5 BV/h, then the proportion of methanol in the mobile phase is increased to 12% to elute at the flow rate of 5 BV/h. the on-line detection wavelength $\lambda$=280, the eluent is collected when the absorptive value begins with rising rapidly, to totally collect 10 bottles, one bottle per 2.5 L, and to determine the content of vancomycin B per bottle, and then the eluents with a chromatographic purity of more than 98.5% are mixed to obtain a mixed chromatographic solution of 12.5 L, with the concentration of 6.2 mg/ml, and the mixed chromatographic solution is adjusted to pH=2.8 with 4N hydrochloric acid.

The above chromatographic solution is passed through a nanofiltration membrane with a pore diameter of molecular weight of 400 for desolvation. the mixture solution is concentrated to a concentration of 200 mg/ml and volume of 370 ml when no solvent is produced anymore, and then the concentrate is filtered by a filter membrane of 0.45 μm, and is freeze-dried in a freeze dryer to obtain freeze-dried powders of vancomycin hydrochloride of 60.6 g, the yield of 62.4%, the chromatographic purity of 99.2%, and the absorbance A of solution of 10% is 0.016.

Example 15: Comparison of Different pH in the $CH_3COONH_4$ Systems as Mobile Phase 650 ml of the concentrate with the concentration of 156 mg/ml, chromatographic purity of 95.7% is adjusted to pH=4.0 with hydrochloric acid or sodium hydroxide, is filled into a preparative column (15 cm*30 cm) containing C18 silica gel filler with particle size of 30 μm and is adjusted to pH=4.0 with hydrochloric acid, and pre-washed for 100 min with an aqueous solution containing 0.5% $CH_3COONH_4$ (W/V) and 8% (V/V) methanol aqueous solution as mobile phase, at the flow rate of 5 BV/h, then the proportion of methanol in the mobile phase is increased to 12% to elute at the flow rate of 5 BV/h. the on-line detection wavelength $\lambda$=280, the eluent is collected when the absorptive value begins with rising rapidly, to totally collect 10 bottles, one bottle per 2.5 L, and to determine the content of vancomycin B per bottle, and then the eluents with a chromatographic purity of more than 98.5% are mixed to obtain a mixed chromatographic solution of 12.5 L, with the concentration of 6.4 mg/ml, and the mixed chromatographic solution is adjusted to pH=2.8 with 4N hydrochloric acid.

The above chromatographic solution is passed through a nanofiltration membrane with a pore diameter of molecular weight of 400 for desolvation. the mixture solution is concentrated to a concentration of 200 mg/ml and volume of 385 ml when no solvent is produced anymore, and then the concentrate is filtered by a filter membrane of 0.45 μm, and is freeze-dried in a freeze dryer to obtain freeze-dried powders of vancomycin hydrochloride of 63.9 g, the yield of 63.0%, the chromatographic purity of 99.0%, and the absorbance A of solution of 10% is 0.014.

Example 16: Comparison of Different pH in the $CH_3COONH_4$ System as Mobile Phase 670 ml of the concentrate with the concentration of 145 mg/ml, chromatographic purity of 96.6% is adjusted to pH=4.5 with sodium hydroxide, is filled into a preparative column (15 cm*30 cm) containing C18 silica gel filler with particle size of 30 μm and is adjusted to pH=4.5 with acetic acid, and pre-washed for 100 min with an aqueous solution containing 0.5% $CH_3COONH_4$ (W/V) and 8% (V/V) methanol aqueous solution as mobile phase, at the flow rate of 5 BV/h, then the proportion of methanol in the mobile phase is increased to 12% to elute at the flow rate of 5 BV/h. the on-line detection wavelength $\lambda$=280, the eluent is collected when the absorptive value begins with rising rapidly, to totally collect 10 bottles, one bottle per 2.5 L, and to determine the content of vancomycin B per bottle, and then the eluents with a chromatographic purity of more than 98.5% are mixed to obtain a mixed chromatographic solution of 12.5 L, with the concentration of 6.1 mg/ml, and the mixed chromatographic solution is adjusted to pH=2.8 with 4N hydrochloric acid.

The above chromatographic solution is passed through a nanofiltration membrane with a pore diameter of molecular weight of 400 for desolvation. the mixture solution is concentrated to a concentration of 200 mg/ml and volume of 370 ml when no solvent is produced anymore, and then the concentrate is filtered by a filter membrane of 0.45 μm, and is freeze-dried in a freeze dryer to obtain freeze-dried powders of vancomycin hydrochloride of 61.0 g, the yield of 62.8%, the chromatographic purity of 99.1%, and the absorbance A of solution of 10% is 0.018.

It can be found from comparison of examples 14, 15 and 16 that the pH is controlled between 3.5~4.5 in the column solution and the mobile phase, little impact is on the yield and quality of the prepared product.

Example 17: Example of Reverse Phase Preparation with Polymer Filler PS Resin 680 ml of the concentrate with the concentration of 148 mg/ml, chromatographic purity of 95.9% is adjusted to pH=4.0 with sodium hydroxide, is filled into a preparative column (15 cm*30 cm) containing PS adsorption resin with particle size of 20 μm and is adjusted to pH=4.0 with hydrochloric acid, and pre-washed for 100 min with an aqueous solution containing 5% ethanol (V/V) as mobile phase, at the flow rate of 2 BV/h, then the proportion of ethanol in the mobile phase is increased to 10% to elute at the flow rate of 2 BV/h. the on-line detection wavelength $\lambda$=280, the eluent is collected when the absorptive value begins with rising rapidly, to totally collect 10 bottles, one bottle per 2 L, and to determine the content of vancomycin B per bottle, and then the eluents with a chromatographic purity of more than 98.5% are mixed to obtain a mixed chromatographic solution of 12 L, with the concentration of 6.4 mg/ml, and the mixed chromatographic solution is adjusted to pH=2.8 with 4N hydrochloric acid.

The above chromatographic solution is passed through a nanofiltration membrane with a pore diameter of molecular weight of 400 for desolvation. the mixture solution is concentrated to a concentration of 200 mg/ml and volume of 365 ml when no solvent is produced anymore, and then the concentrate is filtered by a filter membrane of 0.45 μm, and is freeze-dried in a freeze dryer to obtain freeze-dried powders of vancomycin hydrochloride of 60.6 g, the yield of 60.2%, the chromatographic purity of 99.3%, and the absorbance A of solution of 10% is 0.016.

Example 18: Example of Reverse Phase Preparation with Polymer Filler PS Resin 680 ml of the concentrate with the concentration of 148 mg/ml, chromatographic purity of 95.9% is adjusted to pH=3.5 with hydrochloric acid, is filled into a preparative column (15 cm*30 cm) containing PS adsorption resin with particle size of 20 μm and is adjusted to pH=3.5 with hydrochloric acid, and pre-washed for 60 min with an aqueous solution containing 5% ethanol (V/V) as mobile phase, at the flow rate of 2 BV/h, then the proportion of ethanol in the mobile phase is increased to 10% to elute at the flow rate of 2 BV/h. the on-line detection wavelength λ=280, the eluent is collected when the absorptive value begins with rising rapidly, to totally collect 10 bottles, one bottle per 2 L, and to determine the content of vancomycin B per bottle, and then the eluents with a chromatographic purity of more than 98.5% are mixed to obtain a mixed chromatographic solution of 12 L, with the concentration of 6.2 mg/ml, and the mixed chromatographic solution is adjusted to pH=2.8 with 4N hydrochloric acid.

The above chromatographic solution is passed through a nanofiltration membrane with a pore diameter of molecular weight of 400 for desolvation. the mixture solution is concentrated to a concentration of 200 mg/ml and volume of 370 ml when no solvent is produced anymore, and then the concentrate is filtered by a filter membrane of 0.45 μm, and is freeze-dried in a freeze dryer to obtain freeze-dried powders of vancomycin hydrochloride of 61.2 g, the yield of 60.8%, the chromatographic purity of 99.0%, and the absorbance A of solution of 10% is 0.015.

Example 19: Example of Reverse Phase Preparation with Polymer Filler PS Resin 650 ml of the concentrate with the concentration of 158 mg/ml, chromatographic purity of 96.2% is adjusted to pH=3.5 with hydrochloric acid, is filled into a preparative column (15 cm*30 cm) containing PS adsorption resin with particle size of 40 μm and is adjusted to pH=3.5 with hydrochloric acid, and pre-washed for 60 min with an aqueous solution containing 5% ethanol (V/V) as mobile phase, at the flow rate of 2 BV/h, then the proportion of ethanol in the mobile phase is increased to 10% to elute at the flow rate of 2 BV/h. the on-line detection wavelength λ=280, the eluent is collected when the absorptive value begins with rising rapidly, to totally collect 10 bottles, one bottle per 2 L, and to determine the content of vancomycin B per bottle, and then the eluents with a chromatographic purity of more than 98.5% are mixed to obtain a mixed chromatographic solution of 12 L, with the concentration of 7.1 mg/ml, and the mixed chromatographic solution is adjusted to pH=2.8 with 4N hydrochloric acid.

The above chromatographic solution is passed through a nanofiltration membrane with a pore diameter of molecular weight of 400 for desolvation. the mixture solution is concentrated to a concentration of 200 mg/ml and volume of 370 ml when no solvent is produced anymore, and then the concentrate is filtered by a filter membrane of 0.45 μm, and is freeze-dried in a freeze dryer to obtain freeze-dried powders of vancomycin hydrochloride of 64.7 g, the yield of 63.0%, the chromatographic purity of 99.0%, and the absorbance A of solution of 10% is 0.012.

Example 20: Example of Reverse Phase Preparation with Polymer Filler PS Resin 650 ml of the concentrate with the concentration of 158 mg/ml, chromatographic purity of 96.2% is adjusted to pH=4.0 with hydrochloric acid, is filled into a preparative column (15 cm*30 cm) containing PS adsorption resin with particle size of 40 μm and is adjusted to pH=4.0 with hydrochloric acid, and pre-washed for 60 min with an aqueous solution containing 5% ethanol (V/V) as mobile phase, at the flow rate of 2 BV/h, then the proportion of ethanol in the mobile phase is increased to 10% to elute at the flow rate of 2 BV/h. the on-line detection wavelength λ=280, the eluent is collected when the absorptive value begins with rising rapidly, to totally collect 10 bottles, one bottle per 2 L, and to determine the content of vancomycin B per bottle, and then the eluents with a chromatographic purity of more than 98.5% are mixed to obtain a mixed chromatographic solution of 12 L, with the concentration of 6.8 mg/ml, and the mixed chromatographic solution is adjusted to pH=2.8 with 4N hydrochloric acid.

The above chromatographic solution is passed through a nanofiltration membrane with a pore diameter of molecular weight of 400 for desolvation. the mixture solution is concentrated to a concentration of 200 mg/ml and volume of 380 ml when no solvent is produced anymore, and then the concentrate is filtered by a filter membrane of 0.45 μm, and is freeze-dried in a freeze dryer to obtain freeze-dried powders of vancomycin hydrochloride of 63.5 g, the yield of 61.8%, the chromatographic purity of 99.1%, and the absorbance A of solution of 10% is 0.018.

In the examples 17-20, chromatography is prepared by using polymer reverse phase fillers PS with two specifications, and is prepared by using indifferent pH. It may be shown from results that the differences of the product component, yield and absorbance between them are little, and their effects are better.

The present invention illustrates by the above examples, however, it is understood that, the present invention is not limited to special instance and implementation scheme described herein. Here the purpose including these special instances and implementation schemes is aimed at helping the persons skilled in the art to achieve this invention. It is easy for any persons skilled in the art to carry out further improvement and perfection not from the spirit and scope of the invention, so the present invention is just limited by the content and scope of claims of the present invention, its intention to cover all included all alternative solutions and equivalent solutions within the spirit and scope of the present invention limited by the appendix claims.

We claim:

1. A method of separation and purification for vancomycin hydrochloride with high purity, comprising the following steps:
    (1) obtaining a vancomycin hydrochloride solution from a crude vancomycin product by ion exchange chromatography and obtaining a first vancomycin hydrochloride concentrate by nanofiltration, desalination and concentration; wherein a filler of the ion exchange chromatography column is a cation exchange glucan gel or agarose gel, a mobile phase is salt-water;
    (2) adjusting the first vancomycin hydrochloride concentrate with a hydrochloric acid solution to pH=3.5-4.5, and then performing a column chromatography using a reverse phase chromatography column for the first vancomycin hydrochloride pH adjusted concentrate, wherein a stationary phase is polystyrene, and a mobile phase is methanol aqueous solution or ethanol aqueous solution, wherein a proportion of methanol or ethanol in the mobile phase is 10% (V/V);
    (3) collecting a chromatographic solution of content of vancomycin hydrochloride of more than 98.5% purity;
    (4) adjusting the chromatographic solution with hydrochloric acid to pH=2.5-3.5, and separating solvent and salt by nanofiltration desalination and concentration to obtain a second vancomycin hydrochloride concentrate; and (5) obtaining a vancomycin dry powder with a chromatographic purity of up to 99% and a pure white appearance by dehydrating and drying the second vancomycin hydrochloride concentrate of step (4).

2. The method according to the claim 1, wherein the vancomycin hydrochloride solution of step (1) obtained by ion exchange chromatography has a chromatographic purity of more than 95%.

3. The method according to the claim 1, wherein the concentration of the vancomycin hydrochloride solution of step (1) is 100 mg/ml-200 mg/ml.

4. The method according to the claim 1, wherein the particle size of polystyrene is 20-40 μm.

5. The method according to the claim 1, wherein the mobile phase of step (2) is adjusted to pH=3.5-5.5 with hydrochloric acid or acetic acid.

6. The method according to the claim 1, wherein the nanofiltration membrane with molecular weight of 100-800 Da of step (4) is used for nanofiltration.

7. The method according to the claim 1, wherein the vancomycin hydrochloride powder of step (5) has absorbance of less than 0.02; whiteness of more than 88%; and chromatographic purity of more than 99% when measured at 10 wt. % concentration of vancomycin hydrochloride powder at a wavelength of 450 nm.

* * * * *